United States Patent
Seo et al.

(10) Patent No.: US 7,563,898 B2
(45) Date of Patent: Jul. 21, 2009

(54) IRIDIUM-BASED LUMINESCENT COMPOUNDS HAVING PHENYLPYRIDINE MOIETIES WITH ORGANOSILICON GROUP, AND ORGANIC ELECTROLUMINESCENCE DEVICES USING THE COMPOUNDS AS COLOR-PRODUCING MATERIALS

(75) Inventors: Jeong Dae Seo, Inchon (KR); Chun Gun Park, Seoul (KR); Soon Ki Kwon, Jinju-si (KR); Yun Hi Kim, Jinju-si (KR); Sung Ouk Jung, Jinju-si (KR); Jun Hwan Ahn, Gyeongsangam-do (KR); Hyung Sun Kim, Gyeongsangnam-do (KR)

(73) Assignee: LG Display Co., Ltd., Seoul (KR)

( * ) Notice: Subject to any disclaimer, the term of this patent is extended or adjusted under 35 U.S.C. 154(b) by 480 days.

(21) Appl. No.: 11/240,633

(22) Filed: Oct. 3, 2005

(65) Prior Publication Data
US 2006/0228581 A1 Oct. 12, 2006

(30) Foreign Application Priority Data
Oct. 4, 2004 (KR) ...................... 10-2004-0078721

(51) Int. Cl.
H01L 51/54 (2006.01)
H05B 33/14 (2006.01)
C09K 11/06 (2006.01)

(52) U.S. Cl. ..................... 546/4; 428/690; 428/917; 257/40; 257/E51.044; 313/504; 313/506; 252/301.16; 252/301.18; 252/301.26; 546/2

(58) Field of Classification Search ................ 428/690, 428/917; 313/504, 506; 257/40, E51.044; 246/2, 4; 252/301.16, 301.14, 301.18, 301.21, 252/301.26
See application file for complete search history.

(56) References Cited

U.S. PATENT DOCUMENTS

| | | | |
|---|---|---|---|
| 5,484,922 A * | 1/1996 | Moore et al. | 546/7 |
| 2002/0064681 A1* | 5/2002 | Takiguchi et al. | 428/690 |
| 2003/0059646 A1* | 3/2003 | Kamatani et al. | 428/690 |

FOREIGN PATENT DOCUMENTS

| | | |
|---|---|---|
| JP | 2001-247859 A | 9/2001 |
| JP | 2002-324679 A | 11/2002 |
| JP | 2003-073665 A | 3/2003 |
| JP | 2003-146996 | 5/2003 |
| JP | 2005-327526 A | 11/2005 |

OTHER PUBLICATIONS

Korean Office Action dated Jun. 25, 2007.

* cited by examiner

*Primary Examiner*—Callie E Shosho
*Assistant Examiner*—Michael Wilson
(74) *Attorney, Agent, or Firm*—Holland & Knight LLP

(57) ABSTRACT

Disclosed are iridium-based luminescent compounds having phenylpyridine moieties with an organosilicon group, and organic electroluminescence devices using the compounds as color-producing materials. The luminescent compounds have the structure of Formula 1 below:

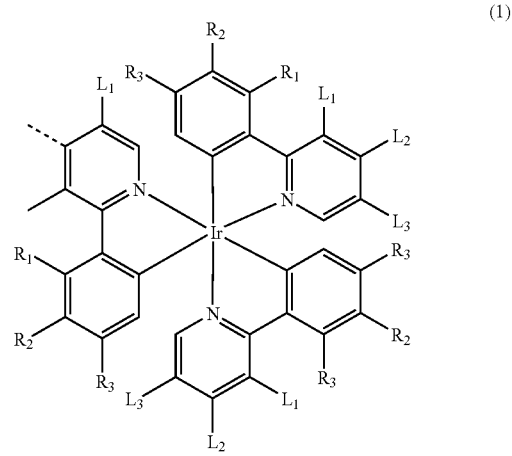

(1)

wherein $L_1$, $L_2$, $L_3$, $R_1$, $R_2$ and $R_3$, which may be identical to or different from each other, are each independently selected from the group consisting of aryl, alkoxy, alkyl, and groups of Formula 3 below:

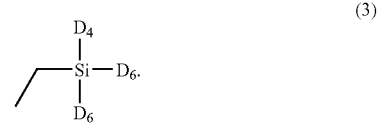

(3)

3 Claims, 6 Drawing Sheets

IRIDIUM-BASED LUMINESCENT COMPOUNDS HAVING PHENYLPYRIDINE MOIETIES WITH ORGANOSILICON GROUP, AND ORGANIC ELECTROLUMINESCENCE DEVICES USING THE COMPOUNDS AS COLOR-PRODUCING MATERIALS

This application claims the benefit of Korean Patent Application No. 10-2004-0078721 filed on Oct. 4, 2004, which is hereby incorporated by reference as if fully set forth herein.

BACKGROUND OF THE INVENTION

1. Field of the Invention

The present invention relates to green light-emitting compounds. More particularly, the present invention relates to iridium-based luminescent compounds having phenylpyridine moieties with an organosilicon group, and organic electroluminescence devices using the compounds as color-producing materials.

2. Discussion of the Related Art

Generally, electroluminescence (EL) devices are self-emissive display devices and are advantageous in terms of broad viewing angle, high contrast, and rapid response time. Such EL devices are classified into inorganic EL devices and organic EL devices according to the kind of materials for the formation of emitter layers. Organic EL devices have excellent luminance, driving voltage and response rate characteristics and easily produce various colors, when compared to inorganic EL devices.

General organic EL devices comprise a substrate, an anode, a hole injecting layer, a hole transport layer, a light-emitting layer, an electron transport layer, and a cathode formed in this order from the bottom. The hole transport layer, the light-emitting layer, and the electron transport layer are organic thin films made of organic compounds.

The fabrication of an organic EL device will be briefly explained below.

(1) First, an anode material is coated on a transparent substrate to form an anode. Indium tin oxide (ITO) is mainly used as the anode material.

(2) A hole injecting layer (HIL) is formed to a thickness of 10~30 nm on the anode. Copper phthalocyanine (CuPc) is mainly used as a material for the hole injecting layer.

(3) A hole transport layer is formed on the hole injecting layer. The hole transport layer is formed by depositing 4,4'-bis[N-(1-naphthyl)-N-phenylamino]-biphenyl (NPB) to a thickness of about 30 nm to about 60 nm on the hole injecting layer.

(4) An organic light-emitting layer is formed on the hole transport layer. If needed, a dopant is added to a material for the organic light-emitting layer. For green light emission, tris(8-hydroxyquinoline aluminum) ($Alq_3$) as a material for the organic light-emitting layer is deposited to a thickness of about 30 nm to about 60 nm on the hole transport layer, and N-methylquinacridone (MQD) is mainly used as a dopant.

(5) An electron transport layer (ETL) and an electron injecting layer (EIL) are sequentially formed on the organic light-emitting layer. Alternatively, an electron injecting/transport layer is formed on the organic light-emitting layer. In the case of green light emission, since $Alq_3$ has superior electron transport ability, the use of the electron injecting/transport layer may be unnecessary.

(6) A cathode material is coated on the electron injecting layer, and finally the resulting structure is covered with a protective film.

The operational principle of the organic EL device having the structure described above is as follows.

When a voltage is applied between the anode and the cathode, holes injected from the anode migrate to the light emitting layer via the hole transport layer while electrons injected from the cathode migrate to the light emitting layer via the electron transport layer. The carriers are recombined with each other in the light emitting layer to form excitons, and then the excitons fall from the excited state to the ground state to allow fluorescent molecules present in the light-emitting layer to emit light, achieving the formation of images.

However, although conventional luminescent compounds that have been used as materials for organic light-emitting layers show superior luminescent properties, there is the disadvantage of poor luminescent efficiency due to triplet-triplet annihilation. Accordingly, there is room for improvement in the efficiency of conventional luminescent compounds.

SUMMARY OF THE INVENTION

Accordingly, the present invention is directed to iridium-based luminescent compounds having phenylpyridine moieties with an organosilicon group and organic electroluminescence devices using the compounds as color-producing materials that substantially obviate one or more problems due to limitations and disadvantages of the related art.

An object of the present invention is to provide luminescent compounds with markedly improved luminescent efficiency.

Another object of the present invention is to provide organic electroluminescence devices using the compounds as color-producing materials.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, luminescent compounds have the structure of Formula 1 below:

Formula 1 wherein $L_1$, $L_2$, $L_3$, $R_1$, $R_2$ and $R_3$, which may be identical to or different from each other, are each independently selected from the group consisting of aryl, alkoxy, alkyl, and groups of Formulae 2 and 3 below:

Formula 2 wherein $D_1$, $D_2$ and $D_3$ are each independently selected from the group consisting of $C_{1~18}$ alkyl, $C_{1~18}$ alkoxy, substituted or unsubstituted $C_{1~18}$ alkyl and allyl, and substituted or unsubstituted $C_{6~18}$ fluorinated alkyl and allyl groups;

Formula 3 wherein $D_4$, $D_5$ and $D_6$ are each independently selected from the group consisting of $C_{1~18}$ alkyl, $C_{1~18}$ alkoxy, substituted or unsubstituted $C_{1~18}$ alkyl and allyl, and substituted or unsubstituted $C_{6~18}$ fluorinated alkyl and allyl groups.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Luminescent compounds of the present invention are represented by Formula 1 below:

(1)

wherein $L_1$, $L_2$, $L_3$, $R_1$, $R_2$ and $R_3$, which may be identical to or different from each other, are each independently selected from the group consisting of aryl, alkoxy, alkyl, and groups of Formulae 2 and 3 below:

(2)

wherein $D_1$, $D_2$ and $D_3$ are each independently selected from the group consisting of $C_{1~18}$ alkyl, $C_{1~18}$ alkoxy, substituted or unsubstituted $C_{1~18}$ alkyl and allyl, and substituted or unsubstituted $C_{6~18}$ fluorinated alkyl and allyl groups;

(3)

wherein $D_4$, $D_5$ and $D_6$ are each independently selected from the group consisting of $C_{1~18}$ alkyl, $C_{1~18}$ alkoxy, substituted or unsubstituted $C_{1~18}$ alkyl and allyl, and substituted or unsubstituted $C_{6~18}$ fluorinated alkyl and allyl groups.

The luminescent compounds of Formula 1 are used as green light-emitting agents and show superior luminescent efficiency. In addition, the luminescent compounds of Formula 1 are useful as color-producing materials for display Devices. Organic electroluminescence devices of the present invention comprise organic films, e.g., light-emitting layers, made of the luminescent compounds of Formula 1. The organic electroluminescence devices of the present invention show markedly improved luminescent efficiency and luminance characteristics, as compared to organic electroluminescence devices using common iridium-based compounds having phenylpyridine moieties.

Among the luminescent compounds of Formula 1, preferred is the organic luminescent compound of Formula 4

(wherein $L_3$ and $R_2$ are trimethylsilane, and $L_1$, $L_2$, $R_1$ and $R_3$ are hydrogen in Formula 1) below:

Formula 4

The compound of Formula 4 is prepared through the following synthesis procedure.

1. Synthesis of Compound (A)

1,3-Dibromobenzene was dissolved in diethyl ether, and then 1.2 equivalents of n-butyl lithium was slowly added thereto at −78° C. The diethyl ether used herein was dried using sodium before use. The reaction mixture was stirred at room temperature for 40 minutes. Thereafter, the reaction mixture was cooled to −78° C., and then 1.2 equivalents of chlorotrimethyl silane were added thereto. The resulting mixture was stirred at room temperature for 10 hours. Water was added to the reaction mixture to quench the reaction. The reaction mixture was extracted using diethyl ether, followed by distillation in vacuo, to afford the compound (A) (yield: 73%).

2. Synthesis of Compound (B)

1,3-Dibromopyridine was dissolved in diethyl ether, and then 1.2 equivalents of n-butyl lithium was slowly added thereto at −78° C. The diethyl ether used herein was dried using sodium before use. The reaction mixture was stirred at room temperature for 40 minutes. Thereafter, the reaction mixture was cooled to −78° C., and then 2 equivalents of triethylborate were added thereto. The resulting mixture was stirred at room temperature for 12 hours. The reaction mixture was slowly poured into a 1N HCl solution, and extracted with ethyl acetate to afford the compound (B) (yield: 35%).

3. Synthesis of Compound (C)

1,3-Dibromopyridine was dissolved in diethyl ether, and then 1.2 equivalents of n-butyl lithium was slowly added thereto at −78° C. The diethyl ether used herein was dried using sodium before use. The reaction mixture was stirred at this temperature for 40 minutes. 1.2 Equivalents of chlorotrimethyl silane were added to the reaction mixture. The resulting mixture was stirred at room temperature for 10 hours. Water was poured into the reaction mixture to quench the reaction. The reaction mixture was extracted using diethyl ether, followed by distillation in vacuo, to afford the compound (C) (yield: 73%).

4. Synthesis of Compound (D)

1.2 Equivalents of the compound (B) and one equivalent of the compound (C) were added to a 2M solution of $K_2CO_3$ (THF) under a stream of nitrogen gas. The reaction mixture was refluxed for 5 hours. The reaction mixture was slowly poured into a 1N HCl solution to quench the reaction, and extracted with diethyl ether, affording the compound (D) (yield: 92%).

5. Synthesis of Compound of Formula 4

Figure 1:
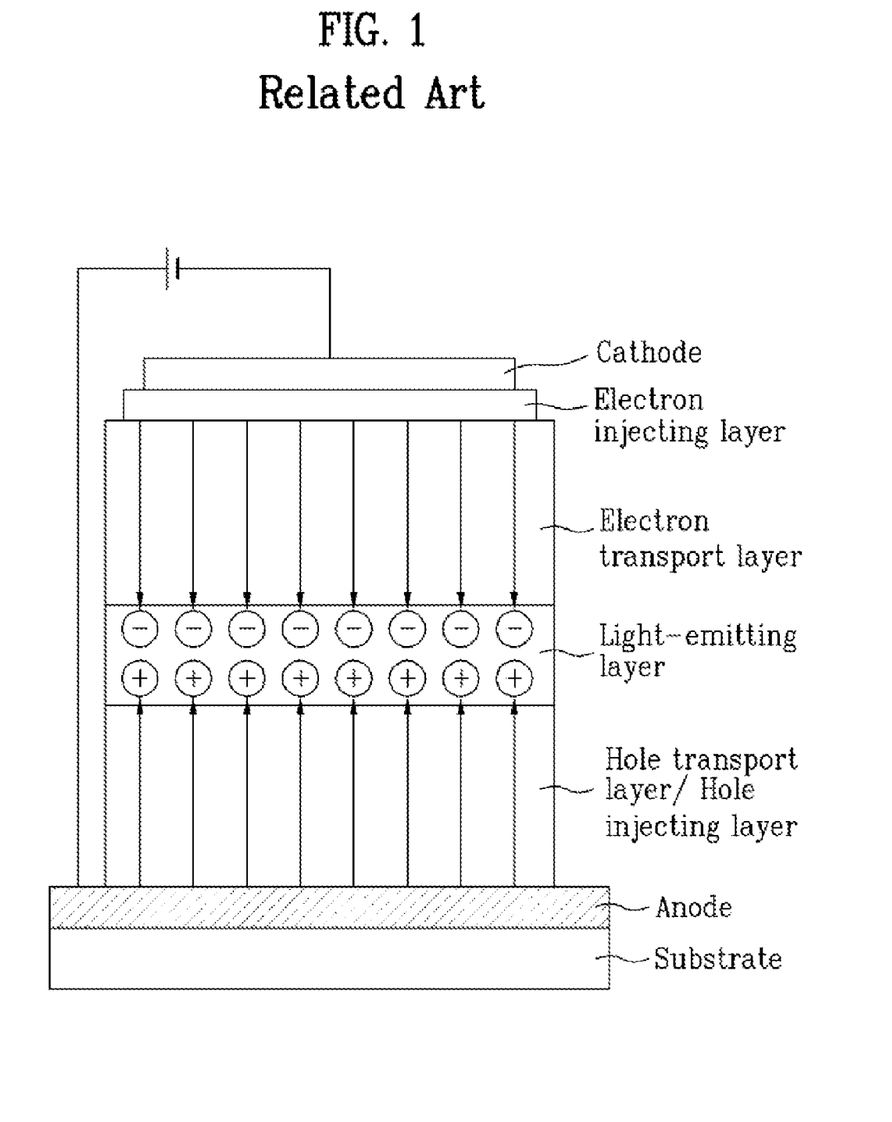
FIG. 1 is a diagram showing the structure of a general OLED.
Figure 2:
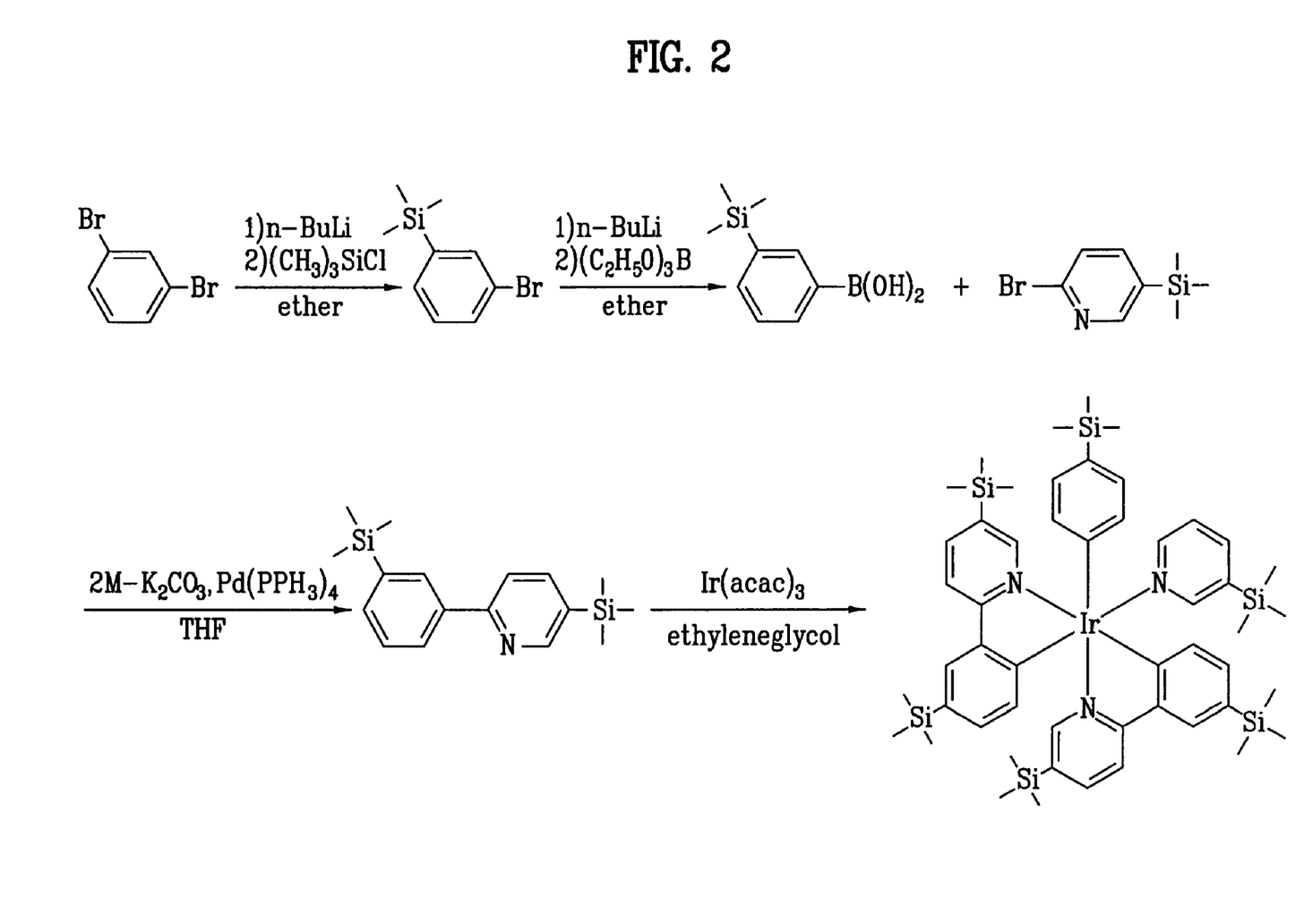
FIG. 2 is a diagram showing the synthesis procedure of the organic luminescent compound represented by Formula 4 according to the present invention.
Figure 3:
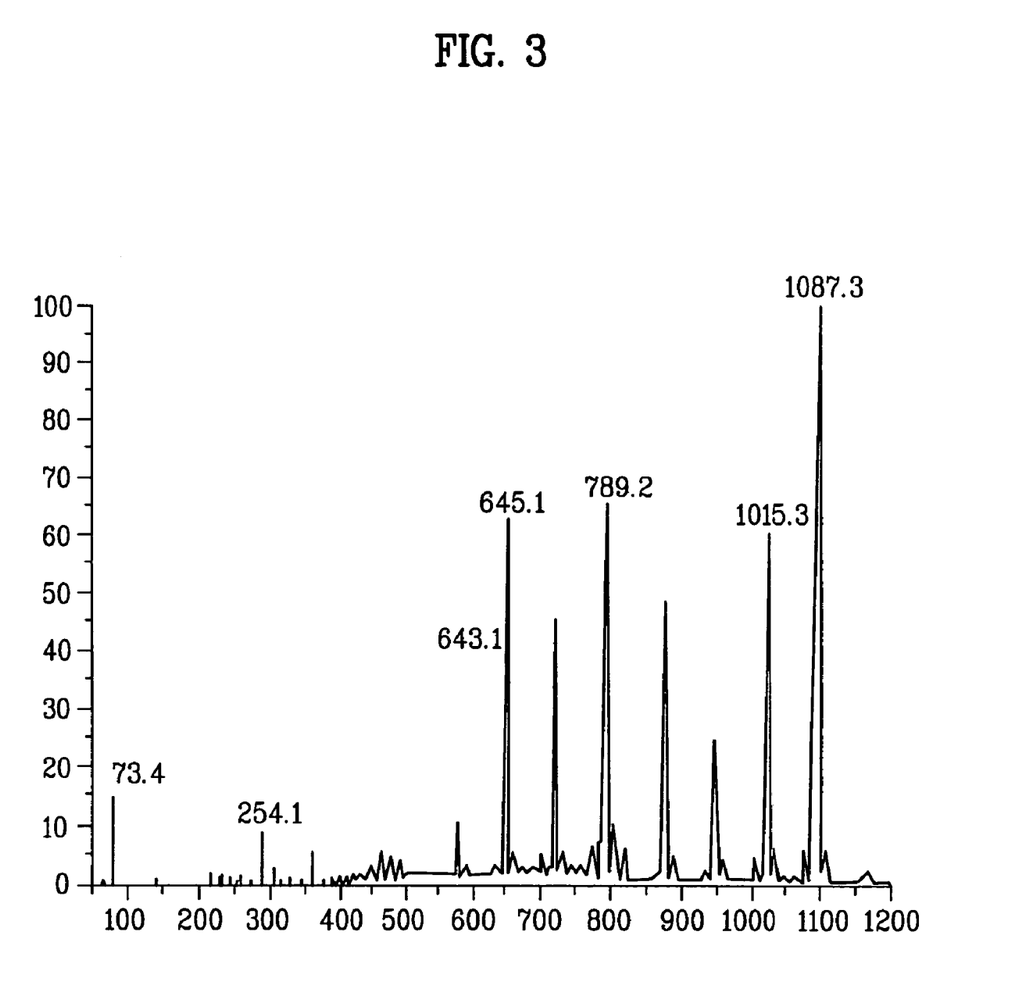
FIG. 3 is a mass spectrum of the organic luminescent compound represented by Formula 4 according to the present invention.
Figure 4:
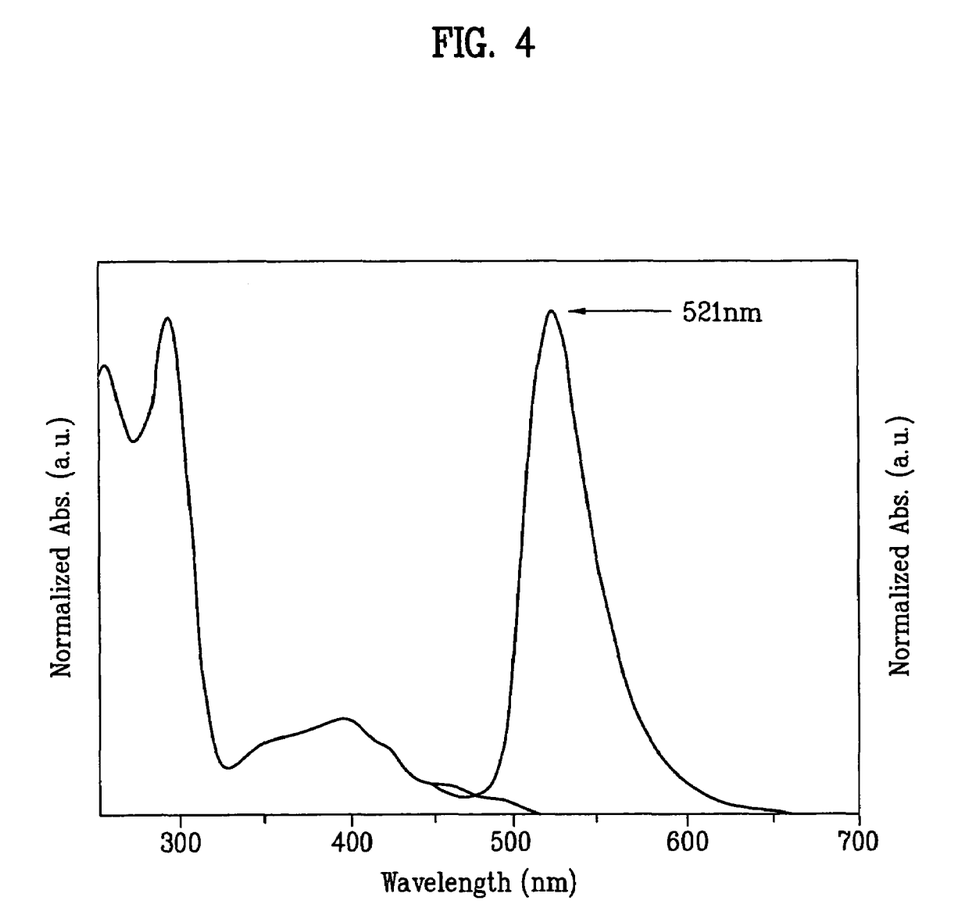
FIG. 4 is a UV/PL spectrum of the organic luminescent compound represented by Formula 4 according to the present invention.

One equivalent of iridium (III) acetylacetonate was added to ethylene glycol under a stream of nitrogen gas. After the mixture was stirred at 80° C. for 30 minutes, 5 equivalents of the compound (D) were added thereto. The resulting mixture was refluxed for 20 hours. The reaction mixture was allowed to cool to room temperature. The reaction mixture was poured into a 1N HCl solution and stirred to obtain a precipitate. The precipitate was filtered, washed with water, and purified by chromatography on silica gel using dichloromethane as an eluting solvent, affording the compound of Formula 4 (yield:

24%). The structure of the compound of Formula 4 was identified by mass spectrometry. The mass spectrum is shown in FIG. 3.

EXAMPLE 5

Indium tin oxide (ITO) was coated on a glass substrate, patterned so that the light-emitting area was 3 mm×3 mm, and washed. After the substrate was placed in a vacuum chamber at a basic pressure of $1 \times 10^{-6}$ torr, CuPC (200 Å), NPB (400 Å), a light-emitting layer (200 Å), BCP (100 Å), Alq$_3$ (200 Å), LiF (5 Å), and Al (1000 Å) were deposited in this order on the ITO to fabricate an OLED. The light-emitting layer was formed by depositing CBP as a host and the compound of Formula 4 (8%) as a dopant. The OLED was measured to have a driving voltage of 9.71V, a luminance of 955 nits and a color coordinate (0.316, 0.603) at 11.1 mA/cm$^2$.

Figure 5:
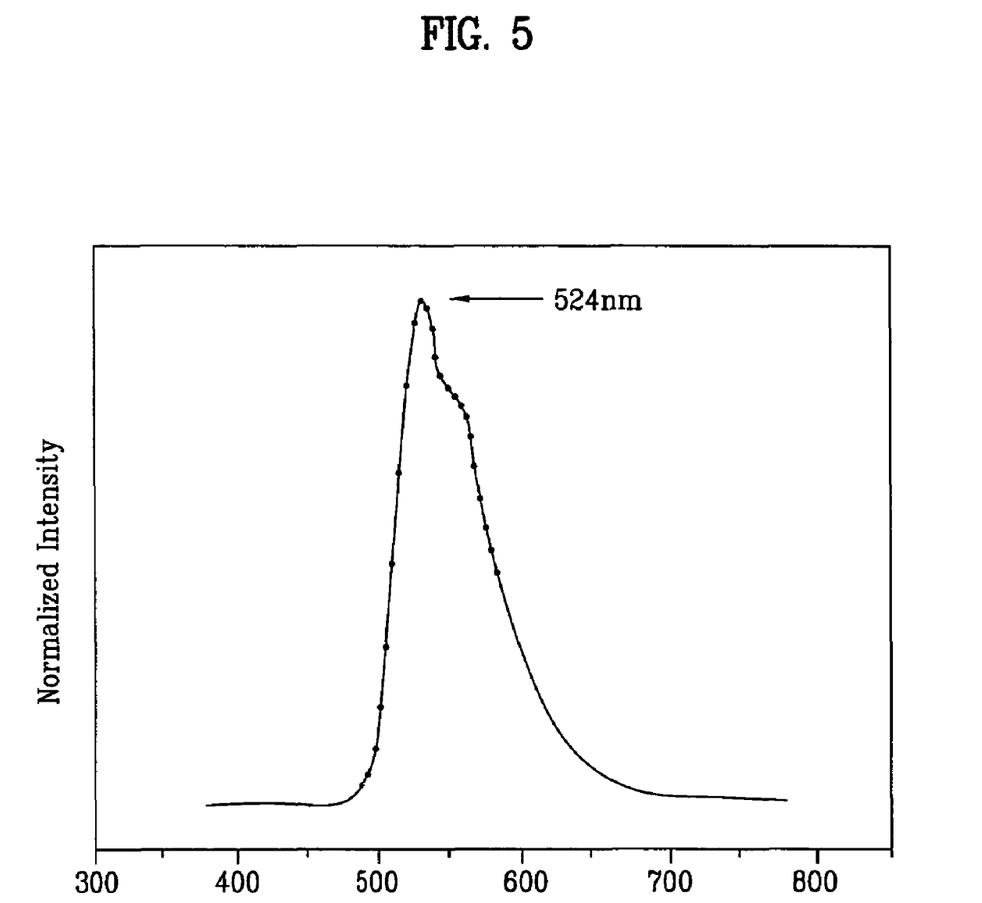
FIGS. 5 and 6 are graphs showing the characteristics of an OLED wherein the organic luminescent compound represented by Formula 4 according to the present invention is used as a material for a light-emitting layer.
Figure 6:
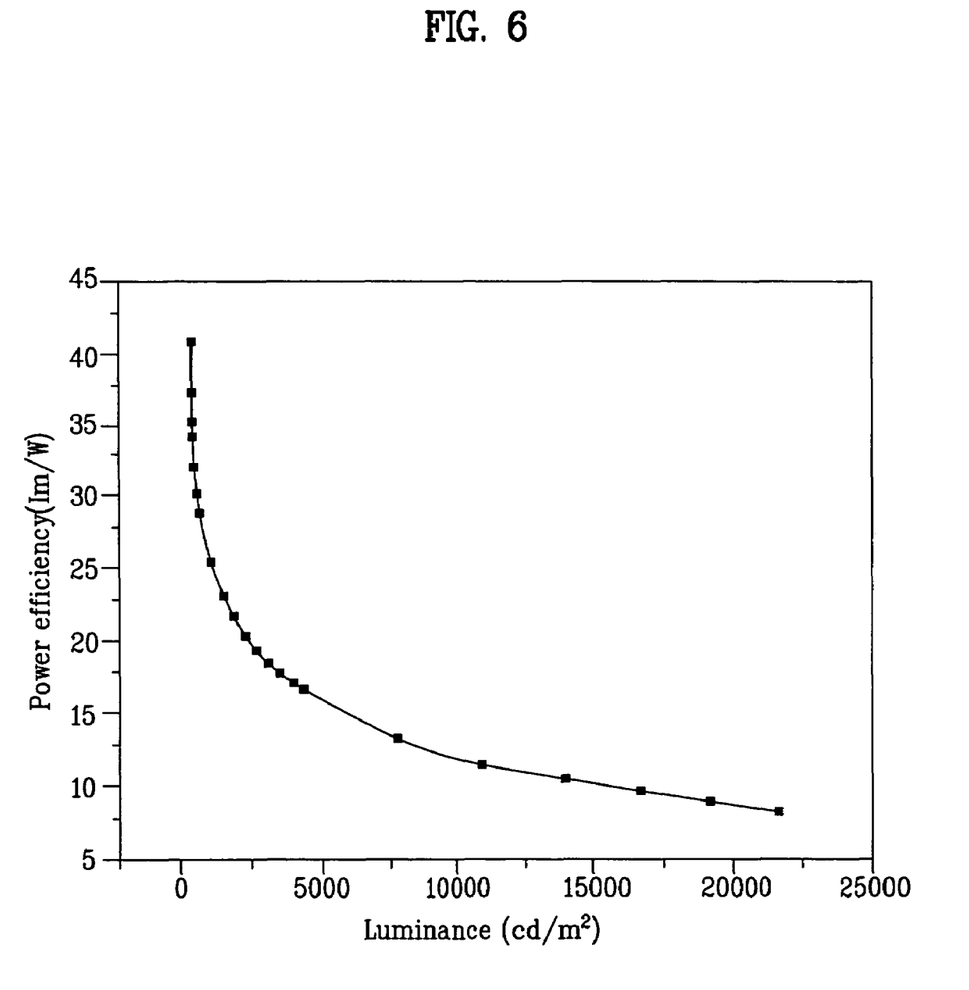

The graphs shown in FIGS. 5 and 6 indicate that the OLED of the present invention shows superior luminescent properties.

The luminescent compound of the present invention show markedly improved luminescent efficiency, and the OLED using the luminescent compound as a material for the light-emitting layer show superior luminescent properties, i.e., high external quantum efficiency, high luminance, and low driving voltage.

It will be apparent to those skilled in the art that various modifications and variations can be made in the present invention without departing from the spirit or scope of the inventions.

The scope of the present invention is, therefore, defined by the claims that follow, rather than by the foregoing description.

What is claimed is:

1. An iridium-based luminescent compound of Formula 1 below:

(1)

wherein $L_1$, $L_2$, $L_3$, $R_1$, $R_2$ and $R_3$, which may be identical to or different from each other, are each independently selected from the group consisting of hydrogen, and group of Formula 3 below:

(2)

(3)

wherein $D_4$, $D_5$ and $D_6$ are each independently selected from the group consisting of $C_{1~18}$ alkyl, $C_{1~18}$ alkoxy, substituted or unsubstituted $C_{1~18}$ alkyl and allyl, and substituted or unsubstituted $C_{6~18}$ fluorinated alkyl and allyl groups, wherein at least one of $L_1$, $L_2$, $L_3$, $R_1$, $R_2$ and $R_3$ is not hydrogen.

2. The compound according to claim 1, wherein $L_1$, $L_2$, $R_1$ and $R_3$ are hydrogen, $L_3$ and $R_2$, are the group of Formula 3 below:

(3)

(2)

3. An organic electroluminescence device using the iridium-based luminescent compound according to claims 1 or 2 as a color-producing material.

* * * * *